US00PP21247P2

(12) United States Plant Patent
Kordes

(10) Patent No.: US PP21,247 P2
(45) Date of Patent: Aug. 31, 2010

(54) HYBRID TEA ROSE PLANT NAMED 'KORSOUBA'

(50) Latin Name: *Rosa hybrida*
Varietal Denomination: KORsouba

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/459,102

(22) Filed: Jun. 25, 2009

(51) Int. Cl.
*A01H 5/00* (2006.01)

(52) U.S. Cl. ..... Plt./130
(58) Field of Classification Search ..... Plt./130
See application file for complete search history.

(56) References Cited

OTHER PUBLICATIONS

2008/1239, European Union CVPO summary, Aug. 15, 2008, European Union.

*Primary Examiner*—Susan B McCormick Ewoldt

(57) ABSTRACT

A new and distinct variety of rose with long lasting, novel cream pink flowers, and attractive foliage with good disease resistance. It exhibits uniform, upright to bushy growth with abundant flowers. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida,* 'KORsouba'.

BACKGROUND OF THE INVENTION

The new variety of rose plant of the present invention originated from a controlled crossing made in a rose breeding program between 'TANanilov' and 'NOAsia', both non- patented roses.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORsouba'.

SUMMARY OF THE INVENTION

The new rose plant may be distinguished from its seed parent, 'TANanilov' by the following combination of characteristics:

1. The flower color of 'TANanilov' is pink, while the flower color of 'KORsouba' is cream pink.
2. The fragrance of 'TANanilov' is strong, while the fragrance of 'KORsouba' is moderate.

The new rose plant may be distinguished from its pollen parent, NOAsia' by the following combination of characteristics:

1. The flower color of 'NOAsia' is pink, while the flower color of 'KORsouba' is cream pink.
2. The petal count of 'NOAsia' is semi-double, while the petal count of 'KORsouba' is very double.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORsouba' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORsouba' was selected in May, 2000 from the seedling beds to be asexually propagated for further evaluation. The first asexual propagation of 'KORsouba' was done by budding to seedling understocks in August, 2000 at the inventor's nursery in Offenseth-Sparrieshoop, Germany.

This initial and other subsequent propagations conducted in controlled environments demonstrate that 'KORsouba' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, leaves, and stems of 'KORsouba'.

DETAILED BOTANICAL DESCRIPTION

The following is a description of 'KORsouba', as observed growing in October, 2008 in a nursery in Jackson County, Oreg. on plants of 30 months of age. Color references are made using The Royal Horticultural Society (London, England) Colour Chart, 2001 except where common terms of color are used.

For a comparison, several physical characteristics of the rose variety 'KORaburg', a rose variety from the same inventor described and illustrated in U.S. Plant Pat. No. 17,763 and issued on May 29, 2007 are compared to 'KORsouba' in Chart 1.

CHART 1

| Characteristic | 'KORsouba' | 'KORaburg' |
|---|---|---|
| Flower, general tonality | Orange-White Group 159C | Red-Purple Group 58C |
| Flower size, when open | 100-120 mm | 100-120 mm |
| Overall plant height | 120-125 cm | 120 cm |

Parents:

*Seed parent.*—'TANanilov'.

*Pollen parent.*—'NOAsia'.

Classification:

*Botanical classification.*—*Rosa hybrida,* 'KORsouba'.

*Commercial classification.*—Hybrid Tea.

FLOWER AND FLOWER BUD

*Blooming habit.*—Recurrent.

*Flower bud.*—Size: Upon opening, 35 mm in length from base of receptacle to end of bud and 27 mm diameter at its widest point. Bud form: Long. Pointed ovoid. Bud color: As sepals first unfold, bud color is Yellow-Green Group 150D. When ¼ open, the upper surface of petals is Yellow Group 10D and the lower surface is Yellow Group 11C with intonations of Red Group 54A on petal margins.

*Sepals.*—Size: Average 25-28 mm long×8-9 mm wide. Shape: Sepals generally subulate. Sepal apex is generally cirrose. Weak foliaceous appendages on three of the five sepals. Base is flat at union with receptacle. Quantity: Five. Margins: With stipitate glands. Surface texture: Inner side: Covered in fine white hairs. Outer surface: smooth. Stipitate glands are absent. Color: Upper surface Yellow-Green Group 150D. Lower surface Yellow-Green Group 144A.

*Receptacle.*—Surface: Smooth. Color: Green Group 143B. Shape: Pear shaped. Size: 10-11 mm (h)×11-12 mm (w).

*Peduncle.*—Surface: Smooth. Length: 40-50 mm average length. Diameter: 4-5 mm average diameter. Color: Yellow-Green Group 144B. Strength: Strong. Borne: Singly. 1-3 buds per flowering stem.

Flower bloom:

*Fragrance.*—Moderate to strong fragrance.

*Duration.*—On the plant 7 days. Long lasting. As a cut flower, 6 to 7 days. Senesced petals drop away cleanly.

*Size.*—Large flowered garden rose. When open, the average flower diameter is 100-120 mm and the average flower height is 50-55 mm.

*Form.*—Shape of flower when viewed from the side: Upon opening, upper part: Flat. Upon opening, lower part: Flattened convex. Open flower, upper part: Flat. Open flower, lower part: Concave.

Color:

*Upon opening, petals.*—Outermost petals: Outer side: Yellow Group 11C with intonations of Red Group 54A. Inner side: Yellow Group 10D. Innermost petals: Outer side: Orange-White Group 159B with intonations of Red Group 54A. Inner side: Yellow-White Group 158A with intonations of Red Group 38A.

*Upon opening, basal petal spots.*—Basal petal spot, outermost petals: Outer side: Yellow Group 2C. Inner side: Yellow Group 2B. Basal petal spot, innermost petals: Outer side: Yellow Group 2B. Inner side: Green-Yellow Group 1A.

*After opening, petals.*—Outermost petals: Outer side: Yellow Group 4D with intonations of Red Group 54A. Inner side: Yellow Group 4D with intonations on petal edges of Red Group 54B. Innermost petals: Outer side: Yellow Group 4D with intonations of Red Group 54B. Inner side: Yellow Group 4D with intonations on petal edges of Red Group 54C.

*After opening, basal petal spots.*—Basal petal spot, outermost petals: Outer side: Yellow Group 2C. Inner side: Yellow Group 2C. Basal petal spot, innermost petals: Outer side: Yellow Group 2C. Inner side: Yellow Group 2C.

*Variegations.*—None.

General tonality: On open flower Orange-White Group 159C. No change in the general tonality at the end of the 5$^{th}$ day. Afterwards, general tonality is White Group 155A.

Petals:

*Petal count.*—Approximately 40-45 petals under normal conditions.

*Petal reflex.*—Petals reflex slightly.

*Petal edge.*—Ruffled.

*Petal shape.*—Deltoid. Apex shape is round. Shape of base is acute.

*Petal size.*—50-55 mm long; 45-50 mm wide.

*Thickness.*—Thick.

*Petal arrangement.*—Generally in a regular pattern with overlapping edges.

Petaloids: Present.

*Petaloid count.*—Average of 2-4 per flower.

*Petaloid edge.*—Ruffled.

*Petaloid texture.*—Smooth.

*Petaloid shape.*—Linear to elliptic.

*Petaloid size.*—Petaloids are 14-16 mm long and 5-6 mm wide.

*Petaloid color.*—Color of inner side is Red Group 49B and Red Group 49C. Color of outer side is Orange-White Group 159C with intonations on petaloid edges of Red Group 54A.

Reproductive organs:

*Pistils.*—Approximately 35-40 present. Stigmas: Location: Slightly superior in position to anthers. Color: Yellow-White Group 158C. Styles: Length: 10-11 mm long. Color: Red-Purple Group 58A. Intonations of Greyed-Yellow Group 162D.

*Stamens.*—Approximately 70-80 on average and regularly arranged. Anthers: Size: 3 mm long. Color: Yellow Group 13A and Yellow Group 13B. Pollen: Absent. Filaments: Color: Red Group 51C with intonations of Yellow-Green Group 154D. Length: 9-10 mm.

THE PLANT

*Plant growth.*—Vigorous. Upright to bushy habit. When grown as a budded nursery plant the average plant height is 120-125 cm and the average plant width is 75-85 cm.

*Stems.*—Stem color: Young wood: Yellow-Green Group 146B. Anthocyanin: Greyed-Purple Group 183A and 183B. Older wood: Green Group 137C. Stem surface: Young wood: Smooth. Older wood: Rough.

*Prickles.*—Present. Incidence: 10-12 per 10 cm of stem. Size: Average length: 8-10 mm. Color: Immature prickles: Greyed-Purple Group 184A. Mature prickles: Greyed-Orange Group 166A. Senescing to Greyed-Orange Group 166A. Shape: Concave. Anthocyanin: Color: Greyed-Purple Group 184A.

*Leaves and leaflets.*—Normally 3-5 leaflets on normal leaves in middle of the stem. Leaf size: 150-180 mm (1)×120-140 mm (w). Quantity: Abundant. Texture: Upper side of leaflet: Semi-glossy. Leathery. Under side of leaflet: Matte. Rough. Leathery. Color, mature foliage: Upper Leaf Surface: Yellow-Green Group 147A. Lower Leaf Surface: Yellow-Green Group 148B. Color, juvenile foliage: Upper Leaf Surface: Green Group 137A. Lower Leaf Surface: Yellow-Green Group 148B. Anthocyanin intonation: Present. Location: Intonations present on juvenile leaf margins, developing leaves, peduncles, rachis, petiole, and stems. Color: Greyed-Purple Group 187A.

*Stipules.*—Size: 18-20 mm long. 10-11 mm between the tips of the stipule. Main body of stipule 5-6 mm in width. Shape: Longitudinally flanged or winged along middle. Stipule color: Green Group 138A and Yellow Group 146B. Anthocyanin: Greyed-Purple Group 184B. Presence of stipitate glands: Present on margins. Margins: Serrated. With stipitate glands.

*Petiole.*—Length: 15-20 mm. Diameter: 1.5-2.0 mm. Petiole color: Green Group 138A. Anthocyanin present on juvenile tissue, Greyed-Purple Group 183A. Underneath: Smooth. Stipitate glands: Limited numbers of stipitate glands on margins.

*Petiole rachis.*—Length: 22-25 mm. Diameter: 1.5-2.0 mm. Color: Green Group 138A. Anthocyanin present on juvenile tissue, Greyed-Purple Group 183A. Margins: Stipitate glands present. Prickles: Lacking. Stipitate glands: Limited numbers of stipitate glands on margins.

*Leaflets.*—Size: Average size of the terminal leaflet is 70-80 mm (1)×45-50 mm (w). Shape: Ovate. Base: Broadly ovate. Apex: Acute. Margins: Serrated. Texture: Thick and leathery.

Hips/seed formation: None observed.

Winter hardiness: To date, the variety has been grown successfully in USDA Hardiness Zone 5.

Disease resistance: Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant as herein illustrated and described:

(a) Forms attractive, long lasting cream pink flowers;

(b) Exhibits uniform, upright to bushy growth habit;

(c) Propagates well using traditional methods, and;

(d) Exhibits very good resistance to disease under normal growing conditions, substantially as herein illustrated and described.

* * * * *

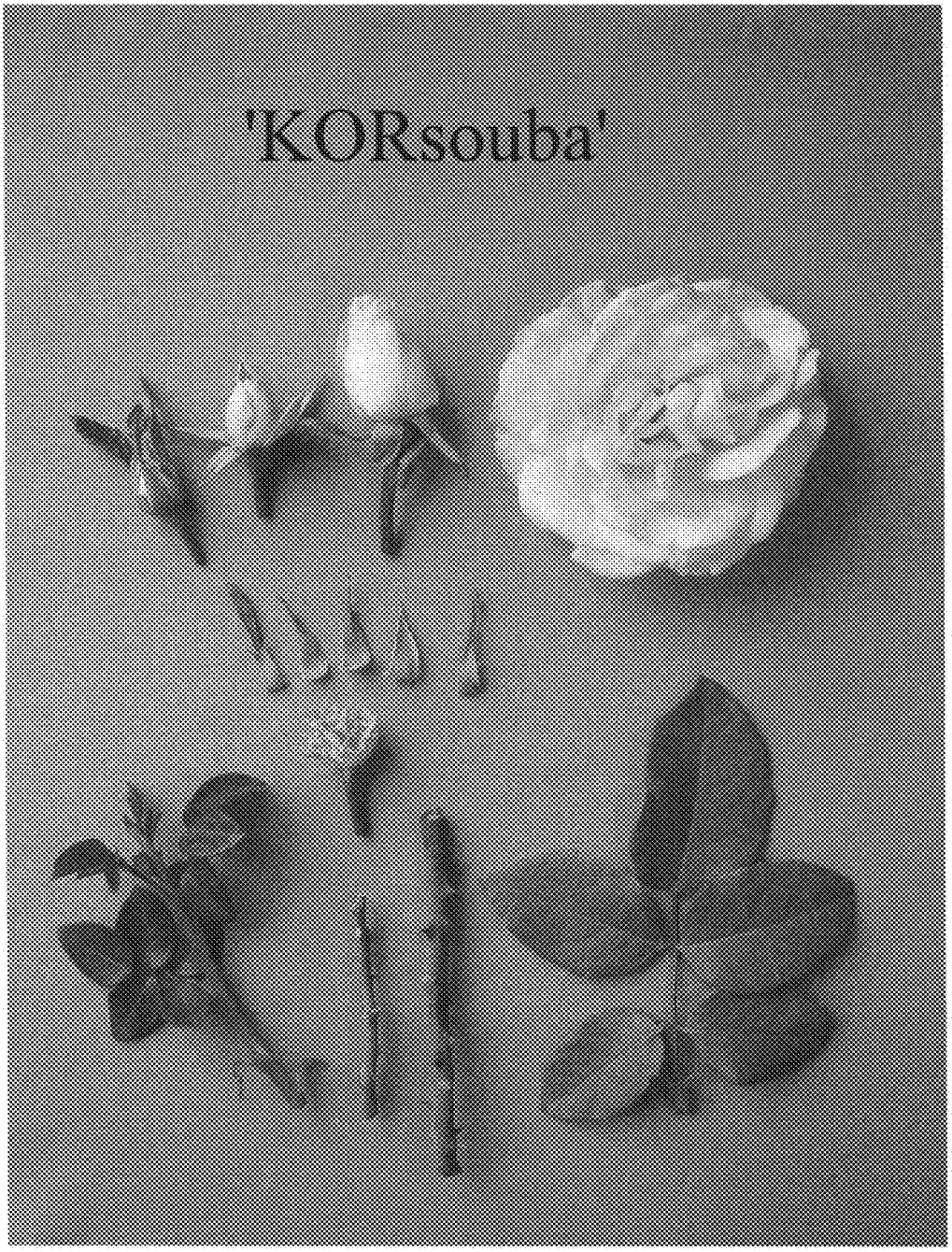
'KORsouba'